United States Patent [19]

Mushabac

[11] Patent Number: 5,569,578
[45] Date of Patent: *Oct. 29, 1996

[54] METHOD AND APPARATUS FOR EFFECTING CHANGE IN SHAPE OF PRE-EXISTING OBJECT

[76] Inventor: David R. Mushabac, 919 Ocean Ave., Brooklyn, N.Y. 11226

[*] Notice: The term of this patent shall not extend beyond the expiration date of Pat. No. 5,562,448.

[21] Appl. No.: 507,162

[22] Filed: Apr. 10, 1990

[51] Int. Cl.$^6$ ................................................. G06F 159/00
[52] U.S. Cl. .............................................. 433/215; 433/27
[58] Field of Search .......................... 364/413.28, 474.01, 364/474.28

[56] References Cited

U.S. PATENT DOCUMENTS

| | | |
|---|---|---|
| 4,436,684 | 3/1984 | White . |
| 4,611,288 | 9/1986 | Duret et al. . |
| 4,663,720 | 5/1987 | Duret et al. . |
| 4,763,791 | 8/1988 | Halverson et al. . |
| 4,837,732 | 6/1989 | Brandestini et al. . |
| 4,936,862 | 6/1990 | Walker et al. . |
| 4,937,928 | 7/1990 | Vanderzel .............................. 433/223 |
| 4,941,826 | 7/1990 | Loran et al. ........................... 433/223 |
| 5,027,281 | 6/1991 | Rekow et al. ...................... 364/474.24 |

Primary Examiner—Gail O. Hayes
Attorney, Agent, or Firm—McAulay Fisher Nissen Goldberg & Kiel, LLP

[57] ABSTRACT

A system for effecting a desired modification in the shape of a pre-existing object to which access is restricted comprises, in accordance with the present invention, a computer, a first data generating device, a second data generating device, a display, an instruction input device and an output device. The first data generating device is operatively connected to the computer for providing the computer with electrically encoded data specifying a three-dimensional surface of the object, while the second data generating device is operatively connected to the computer for providing the computer with electrically encoded data specifying a curvilinear contour of the object. The display is responsive to signals from the computer for displaying a three-dimensional graphic representation of the object in accordance with data from the first data generating device and the second data generating device. The instruction input device operatively serves for instructing the computer to modify the three-dimensional representation of the object on the display and for selecting a modification of the three-dimensional representation which represents a desired object preparation. The output device is operatively coupled to the computer for issuing an output signal to effectuate a limitation in motion of a preparation instrument relative to the object so that the object is provided with the desired object preparation.

77 Claims, 7 Drawing Sheets

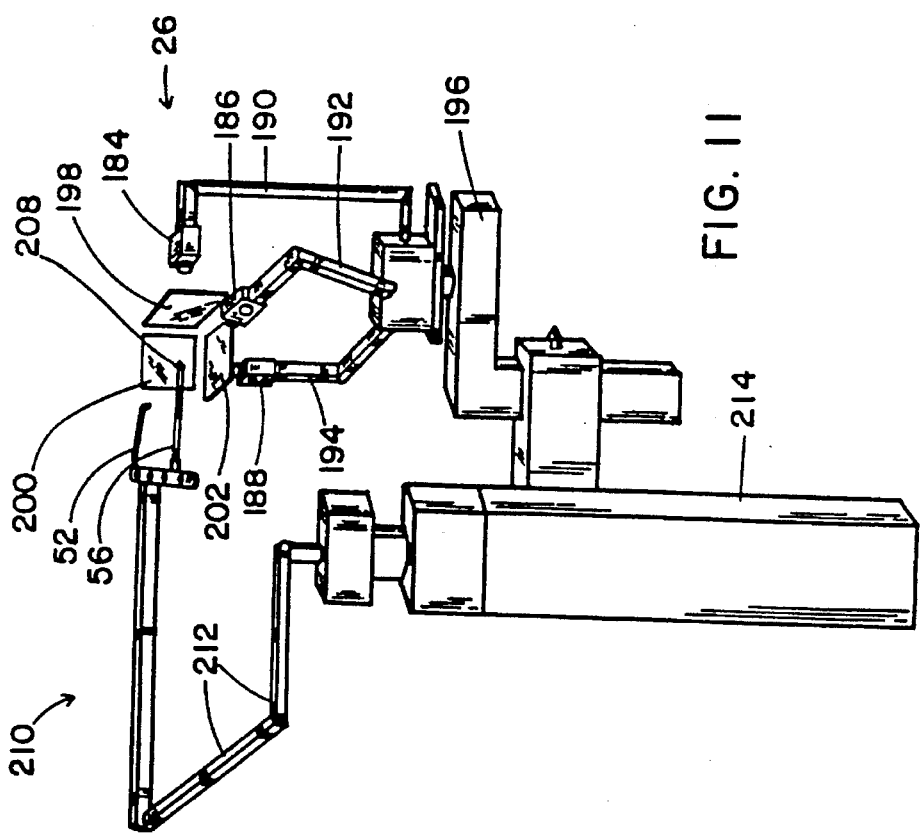
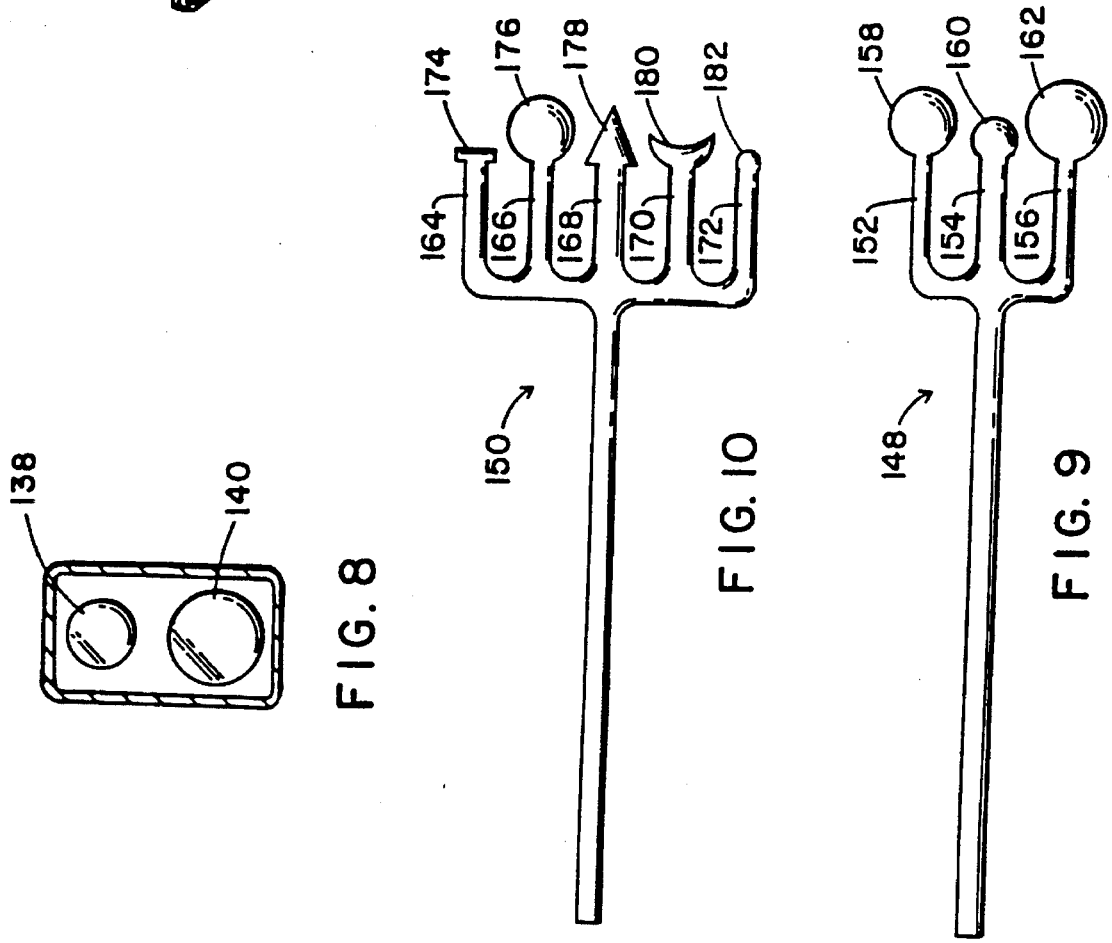
FIG. 8
FIG. 9
FIG. 10
FIG. 11

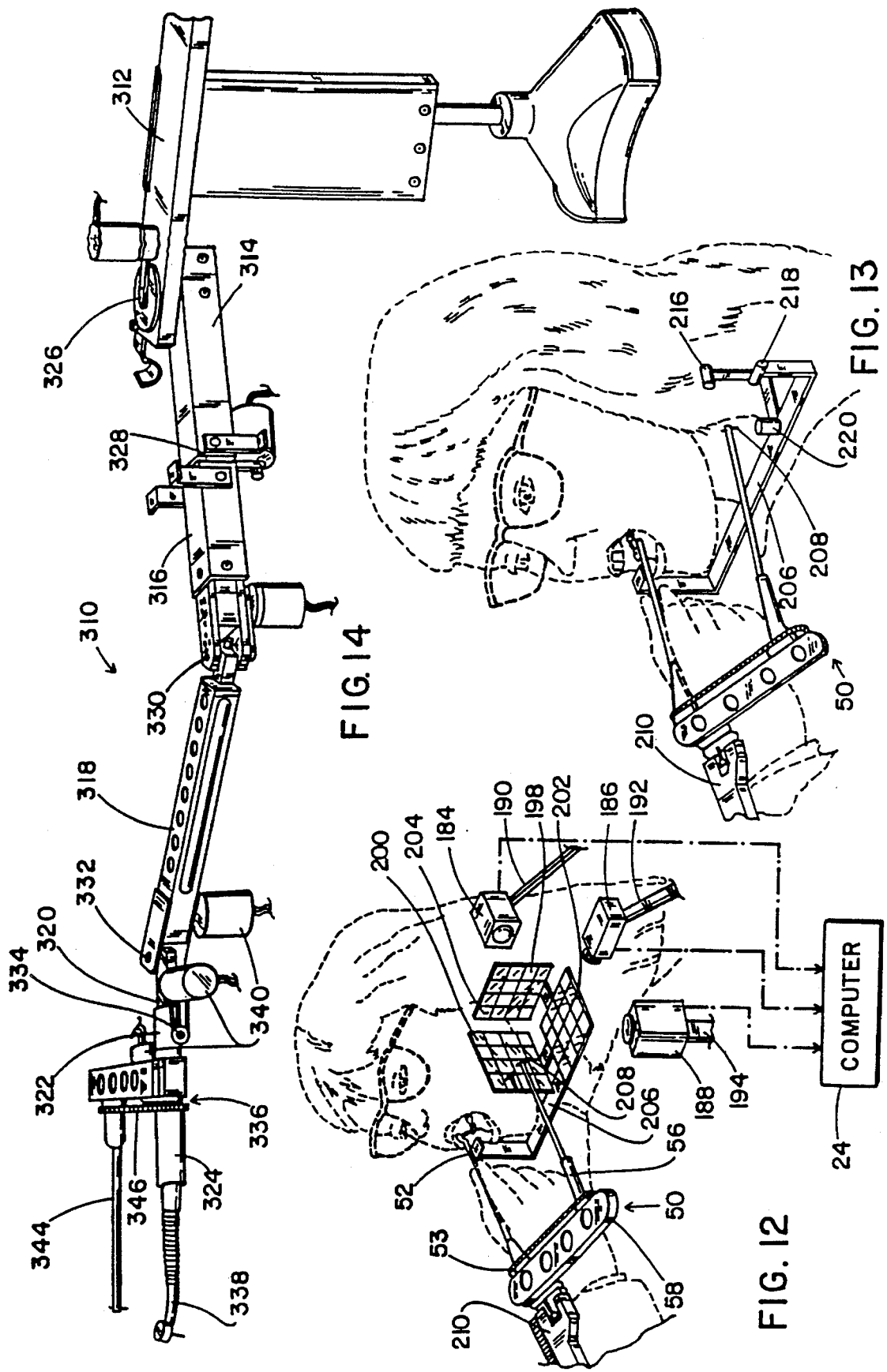

5,569,578

METHOD AND APPARATUS FOR EFFECTING CHANGE IN SHAPE OF PRE-EXISTING OBJECT

BACKGROUND OF THE INVENTION

This invention relates to a method and a system for effecting a desired modification in the shape of a pre-existing object to which access is restricted. This invention also relates to an instrument connectable to a computer for providing said computer with electrically encoded data specifying a three-dimensional surface of an object. In addition this invention relates to a device operably connectable to a computer for providing the computer with electrically encoded data specifying a curvilinear contour of an object. More particularly, this invention relates to a dentistry system.

This invention relates further to a method for generating an electronic representation of a three dimensional surface and to a method for providing a computer with electrically encoded data specifying a three-dimensional surface of an object. The invention is also directed to a method for providing a computer with electrically encoded data specifying a curvilinear contour of a movable object and to a method for effecting a dental preparation.

Computerized control of machining operations is a well established technology. It has been applied to the dental field in controlling the preparation of tooth inlays and onlays such as fillings, crowns and bridges. In accordance with the known technique, a computer is provided with electrically encoded information specifying the surfaces of a prepared tooth. The computer then controls the machining, from a blank, for an inlay, crown or other restoration for insertion into or placement onto the already prepared tooth.

Except for a few such advances in the field, dentistry remains in practice very much in the technological state that it assumed decades ago. Although there have been many improvements in materials, techniques and instrumentation have not generally progressed to keep pace with the computer age.

OBJECTS OF THE INVENTION

An object of the present invention is to provide a method and a system for effecting a desired modification in the shape of a pre-existing object to which access is restricted. Such a method and system would be particularly useful in the field of dentistry for facilitating the preparation of a tooth for receiving a filling, a crown or other inlay or onlay.

Another object of the present invention is to provide an improved method and apparatus for providing a computer with three-dimensional surface data of an object such as a tooth.

Yet another object of the present invention is to provide an improved method and apparatus for providing a computer with three-dimensional contour data of an object such as a tooth.

An additional object of the present invention is to provide a computer interactive system for facilitating dental work.

A further object of the present invention is to provide a dental method and an associated system with an automated safety factor during use of a dental drill and/or other hand-held instruments.

Yet a further object of the present invention is to provide such a dental system which is easy to use, which is capable of simulating treatment, and which enhances diagnosis and the provision of dental care.

SUMMARY OF THE INVENTION

A system for effecting a desired modification in the shape of a pre-existing object to which access is restricted comprises, in accordance with the present invention, a computer, a first data generating device, a second data generating device, a display, an instruction input device and an output device. The first data generating device is operatively connected to the computer for providing the computer with electrically encoded data specifying a three-dimensional surface of the object, while the second data generating device is operatively connected to the computer for providing the computer with electrically encoded data specifying a curvilinear contour of the object. The display is responsive to signals from the computer for displaying a three-dimensional graphic representation of the object in accordance with data from the first data generating device and the second data generating device. The instruction input device operatively serves for instructing the computer to modify the three-dimensional representation of the object on the display and for selecting a modification of the three-dimensional representation which represents a desired object preparation. The output device is operatively coupled to the computer for issuing an output signal to effectuate a limitation in motion of a preparation instrument relative to the object so that the object is provided with the desired object preparation.

A system in accordance with the present invention is especially useful in the field of dentistry. The system facilitates the preparation of a tooth for a filling, a crown or inlay or other restoration. The system works in cooperation with a dentist to optimize a tooth preparation and to maximize the safety accorded to the patient.

Pursuant to another feature of the present invention, the first data generating device includes a scanning component for optically scanning the three-dimensional surface of the object and transmitting a video signal of the three-dimensional surface to the computer. More specifically, the first data generating device includes a projection assembly for optically imposing a grid on the object's three-dimensional surface. In using the first data generating device, an operator provides a reference distance at the three dimensional surface being scanned.

The scanning component preferably includes a opto-electric transducer or sensor such as a camera in the form of a charge-coupled device. More preferably, the scanning component includes two such solid-state cameras with respective optical axes oriented at an angle relative to one another. The cameras may, for instance, be disposed on opposite sides of an output end of the grid projection assembly. Alternatively, the sensors themselves may be disposed in an instrument handle or further away from a light input end of the scanning component. In that event, the scanning component includes at the light input end a lens or lenses for collecting light and light guides extending from the lens to the opto-electric transducers.

In an embodiment of the first data generating device particularly useful for dental applications, at least a portion of the scanning component and the grid projection assembly are mounted to an instrument frame, preferably an elongate frame or holder capable of being inserted into a patient's mouth.

A first data generating device in accordance with the present invention presents the computer with optical or video data comprising numbers of pixels in the array of the solid-state sensing elements of a charge-coupled device. The pixels correspond to the distances between features on the three-dimensional surface of the object being scanned. To facilitate the optical data-gathering operation, the computer is provided with a reference distance at the three-dimensional surface. This reference distance may be provided in any of several different ways, including the positioning of a reference marker of known dimensions on the three-dimensional surface. The reference marker advantageously takes the form of a stylus carried by the instrument frame at a distal end thereof. The stylus may be retractably mounted to the frame and be provided at a distal tip with an enlargement or several enlargements of different shapes and/or sizes and known dimensions.

A first data generating device in accordance with the present invention enables an operator such as a dentist to obtain video or optical data from any surface in a patient's mouth or other similarly inaccessible or limitedly accessible location. Two CCD sensors are sufficiently small to be inserted into a patient's mouth, together with the output end of the grid projection assembly.

Pursuant to another feature of the present invention, the second data generating device includes a manipulable stylus-type instrument having a distal tip engageable with the object and further includes a position detection assembly for monitoring the location of the stylus tip relative to the object and for feeding electrically encoded data regarding the stylus tip location to the computer. In a preferred embodiment of the second data generating means, the position detection assembly comprises what is called here a pantograph assembly that functions to duplicate motion. The assembly includes a pantograph extension rigidly connected to the stylus-type instrument and an optical scanner for tracking the location of a point on the pantograph extension and transmitting a resulting video signal to the computer.

The position detection assembly may also incorporate a reference element for enabling the computer to determine, via video signals from the scanner, the location of the point on the pantograph extension relative to the object. Either the reference element or an input element of the scanner is fixed relative to the object. In a specific realization of the invention, the reference element takes the form of a grid fixed relative to the object. In another specific realization of the invention, the optical scanner includes a solid state optical sensor (charge-coupled device) fixed relative to the object.

The second data generating device of a shape modification system in accordance with the present invention enables a dentist or other operator to obtain shape data about areas which are not optically accessible, for example, areas below the gum line of a tooth. Such information is necessary for enabling tooth preparation to extend below the gum line.

Pursuant to another feature of the present invention, the shape modification system further comprises a cutting instrument and a position detection assembly for monitoring the location of a tip of the cutting instrument relative to the object and for feeding data regarding the cutting tip location to the computer. The position detection assembly may take the form described hereinabove with reference to the stylus-type instrument of the second data generating device, i.e., it may include a pantograph extension connected to the cutting instrument and an optical scanner for optically scanning the location of a point on the pantograph extension and transmitting a resulting video signal to the computer.

In a preferred form of the invention, a cutting tool attachment may be substituted for a stylus attachment on a handle, holder or frame member.

A shape modification system in accordance with the present invention may include any display capable of representing a three-dimensional surface to an operator. For example, the display may take the form of a two-dimensional screen or a holographic projector.

Pursuant to a further feature of the present invention, the instruction input device includes a cutting instrument and position detection assembly for monitoring the location of a tip of the cutting instrument relative to the object and for feeding data regarding the location to the computer. The position detection assembly may be of the kind described hereinabove. Using a cutting tool such as a drill enables an operator such as a dentist to feed a desired depth to the computer. The depth is useable by the computer to select and/or calculate a suggested tooth preparation and to show the suggested preparation on the display.

Alternatively or additionally, the instruction input device includes a keyboard connected to the computer and/or a contact sensitive region of the display. In this case, for example, the desired depth of a tooth preparation may be entered numerically. In addition, the operator may inform the computer via the keyboard of the type of tooth preparation which is desired. If a tooth being worked on is to receive a crown, the operator or dentist informs the computer, in one procedure according to the invention, to remove a certain percentage (e.g., 10%) from all top and side surfaces of the tooth to the contour below the gum line defined by the second data generating device.

The instruction input device may alternatively or additionally take the form of a mouse type device used to select among different types of preparations which have been preloaded in electrically encoded form into the computer's data memory and which the computer shows on the display in response to signals from the operator via the keyboard or other input device.

In the event that the system incorporates a cutting instrument having a power supply operatively connected to the computer and a locator for determining the location of an operating tip of the cutting instrument relative to the object, the output device advantageously includes circuitry for terminating power to the cutting instrument. As an alternative or a supplemental feature, the output device includes an indicator for producing an alert signal to an operator. The output circuit is energized by the computer upon detecting that the cutting instrument is approaching a limit or boundary in a selected preparation. The computer requires realtime data, of course, as to the location of the cutting instrument relative to the object (tooth) being cut. This information is preferably supplied by the pantograph and optical scanner assembly described above.

Pursuant to yet a further feature of the present invention, a third data generating device is operatively connected to the computer for providing the computer with electrically encoded data specifying an internal structural feature of the object. Such a data generating device may include an X-ray machine. The data from the third data generating device is used by the computer to show internal structural features, for example, the nerve and dentine of a tooth, on the display. The internal structural features are taken into account by the operator and also by the computer during the selection of a desired preparation. A selected tooth preparation, for example, will maintain a predetermined minimum distance from the tooth nerve (unless circumstances indicate that a root canal is necessary).

A surface data generating instrument preferably comprises, in accordance with a specific embodiment of the present invention, an elongate frame member, a grid projection assembly mounted to the frame member for imposing a grid on a three-dimensional surface and optical scanner assembly also mounted to the frame member for optically scanning the three-dimensional surface and transmitting to a computer a video signal of the three-dimensional surface with a light grid imposed on the surface by the grid projection assembly. The optical scanning assembly includes two optical transmission paths, which in turn are provided with a pair of solid-state sensors (charge-coupled devices). The optical transmission paths have respective optical axes disposed at an angle to one another at input ends of the optical paths, the input ends being disposed at the distal end of the frame member and on opposite sides of an output end of the grid projection assembly. Preferably, the instrument carries a reference element for establishing a reference distance on the three-dimensional surface. The reference element is in the form of a stylus removably or retractably mounted to the frame at the distal end thereof. The stylus advantageously has a plurality of prongs provided at their tips with enlargements of different geometries.

A dentistry system in accordance with a particular feature of the present invention comprises a computer, a data generating device, a display and an instruction input device. The data generating device is operatively connected to the computer for providing the computer with electrically encoded data specifying a three-dimensional surface of a tooth, while the display is operatively connected to the computer for displaying a three-dimensional graphic representation of the tooth in response to signals generated by the computer in accordance with data from the data generating device. The instruction input device is operatively connected to the computer for enabling an operator to instruct the computer to modify the three-dimensional representation of the tooth on the display and to select a modification of the three-dimensional representation which represents a desired tooth preparation.

The instruction input device includes a manipulable dentist's drill and position detection assembly for monitoring the location of a tip of the drill relative to the tooth and for feeding data regarding the location to the computer. Alternatively, or in addition, the instruction input device includes a keyboard connected to the computer, a mouse type pointer and/or a contact sensitive region of the display.

A dentistry system in accordance with another particular feature of the present invention comprises a computer with a data memory, data generating components operatively connected to the computer for enabling the computer to load into the memory electrically encoded data specifying a three-dimensional surface of a tooth provided with a desired preparation, and an output device operatively connected to the computer for issuing an output signal to effectuate a limitation in motion of a tooth preparation instrument relative to the tooth so that the tooth is provided with the desired tooth preparation. Specifically, the dentistry system is provided with a manipulable dentist's drill having a power supply operatively connected to the computer and a locator device operatively connected to the computer for determining the location of an operating tip of the drill relative to the tooth, while the output device includes circuitry for terminating power to the drill under the control of the computer upon a determination by the computer that a limit or boundary of the desired tooth preparation has been reached by the drill. Alternatively or additionally, the output device includes an indicator for producing an alert signal to an operator.

A method in accordance with the present invention for effecting a desired modification in the shape of a pre-existing object (such as a tooth) to which access is restricted by other formations (other teeth, gums, lips, jaws) comprises the steps of (a) generating electrically encoded data specifying a three-dimensional surface of the object, (b) transmitting the electrically encoded data to a computer loaded with a stereophotogrammetic triangulation program, (c) generating electrically encoded data specifying a curvilinear contour of the object, (d) transmitting the electrically encoded data specifying the curvilinear contour to the computer, (e) operating the computer to display a three-dimensional graphic representation of the object in accordance with the electrically encoded data specifying the three-dimensional surface and the curvilinear contour, (f) instructing the computer to modify the three-dimensional representation of the object to show an object preparation, (g) signaling the computer to select a desired object preparation shown in the three-dimensional graphic representation, and (h) operating the computer to generate an output signal to effectuate a limitation in motion of a preparation instrument relative to the object so that the object is provided with the desired object preparation.

Pursuant to another feature of the present invention, the step of generating electrically encoded data specifying a three-dimensional surface of the object includes the step of optically scanning the three-dimensional surface. The electrically encoded data specifying a three-dimensional surface of the object is preferably included in a video signal. Moreover, a grid is advantageously projected onto the three-dimensional surface, while the computer is provided with a reference distance at the three-dimensional surface.

Pursuant to yet another feature of the present invention, the step of generating electrically encoded data specifying a curvilinear contour of the object includes the step of tracing the curvilinear contour with a manipulable stylus-type instrument having a distal tip engageable with the object, the method further comprising the steps of monitoring the location of the stylus tip relative to the object and feeding electrically encoded data regarding the location to the computer. The location of the stylus tip relative to the object may be determined by optically scanning the location of a point on a pantograph extension rigid with the instrument, the electrically encoded location data being included in a resulting video signal transmitted to the computer. The step of monitoring the stylus tip location also includes the step of providing a reference frame for enabling the computer to determine, via video signals generated in the optical scanning step, the location of the point on the pantograph extension relative to the object.

In the event that the object workpiece is a tooth, either the reference frame or an optical scanner is fixed to the patient's jaw wherein the tooth is rooted.

Pursuant to yet a further feature of the present invention, the method for effecting a desired moficiation in the shape of an object also comprises the steps of cutting the object with a cutting instrument, monitoring the location of a tip of the cutting instrument relative to the object, and feeding data regarding the location of the cutting tip to the computer. The step of monitoring specifically includes the steps of monitoring a pantograph extension connected to the cutting instrument and optically scanning the location of a point on the pantograph extension, the step of feeding location data to the computer including the step of transmitting a video signal containing that data to the computer. In accordance with this feature of the invention, the output signal generated by the computer effectuates a limitation in motion of the cutting instrument relative to the object. For example, the signal may serve to cut off the power being supplied to the cutting instrument.

In another step, a reference frame is provided to the computer for enabling the computer to determine, via video signals from the optical scanner, the location of the point on the pantograph extension relative to the object. The reference frame advantageously includes a grid, for example, disposed on a transparent plate. Either the grid or an optical scanner is fixed relative to the object workpiece. For example, the optical scanner may take the form of a solid state optical sensor fixed relative to the object.

Pursuant to an additional specific feature of the present invention, the step of instructing the computer regarding modification of the three-dimensional representation of the object to show an object preparation includes the steps of cutting an incision into the object with a cutting instrument, monitoring the location of a tip of the cutting instrument relative to the object, and feeding data regarding the cutting tip location to the computer.

The step of instructing the computer further includes, in a preferred embodiment of the invention, the step of operating the computer to select an object preparation from among a set of predefined object preparations stored in encoded form in the computer. The computer is operated to display the selected object preparation preform in overlay on the three-dimensional graphic representation of the object. Alternatively or additionally, the step of instructing includes the step of entering commands via a keyboard connected to the computer, using a mouse type device or touching a contact sensitive region of a display device operatively connected to the computer.

In another, optional step in accordance with the present invention, the computer is provided with electrically encoded data specifying an internal structural feature of the object. This data may be generated, for example, by an X-ray device.

A method for generating an electronic representation of a three dimensional surface comprises, in accordance with the present invention, the steps of (a) imposing a grid on the three-dimensional surface, (b) providing a reference distance at the three-dimensional surface, (c) optically scanning the three-dimensional surface from two different directions, (d) transmitting to a computer video signals encoding the three-dimensional surface from the two different directions with the imposed grid, and (e) operating the computer via a stereophotogrammetic triangulation program to generate an image of the three dimensional surface. The grid is preferably optically projected onto the three-dimensional surface along an optical axis, and the two different directions are oriented at an angle to one another on opposite sides of the optical axis at an output end of an optical projection path.

Pursuant to a specific feature of the present invention, the reference distance is provided by placing two marks a known distance apart on the three-dimensional surface. Alternatively, the reference distance is provided by attaching an object of known dimensions to the three-dimensional surface. In yet another alternative step, the reference distance is provided by juxtaposing an object of known dimensions to the three-dimensional surface. The object of known dimensions may take the form of an enlargement or several enlargements of different geometries at a distal end of a stylus.

A method for providing a computer with electrically encoded data specifying a three-dimensional surface of an object, comprises, in accordance with the present invention, the steps of (a) imposing a grid on the three-dimensional surface, (b) optically scanning the three-dimensional surface from two different directions, and (c) transmitting to a computer video signals encoding the three-dimensional surface from the two different directions with the imposed grid.

In an additional step, a reference distance is provided at the three-dimensional surface. In yet another additional step, the computer is operated via a stereophotogrammetic triangulation program to generate an image of the three dimensional surface.

Pursuant to a specific feature of the present invention, the grid is optically projected onto the three-dimensional surface.

A method for providing a computer with electrically encoded data specifying a curvilinear contour of a movable object comprises, in accordance with the present invention, the steps of (a) manipulating an elongate instrument so that a distal end of the instrument is in contact with a surface of the object along the contour, (b) optically monitoring the location of a point on a pantograph extension rigid with the instrument, and (c) transmitting to the computer a video signal including electrically encoded video information on the location of the point. In a further step, a reference frame is provided for enabling the computer to determine, via the video signal, the location of the point on the pantograph extension relative to the object. In yet a further step, exactly one of the reference frame and optical monitoring means is fixed to the object. The reference frame may take the form of a grid attached to the object. Alternatively, the optical monitoring means may include a solid state optical sensor fixed relative to the object.

A method for effecting a dental preparation comprises, in accordance with the present invention, the steps of (a) providing a computer with electrically encoded data specifying a three-dimensional surface of a tooth, (b) operating the computer display a three-dimensional graphic representation of the tooth in accordance with the electrically encoded data, (c) instructing the computer to modify the three-dimensional representation of the tooth on the display to show a tooth preparation, and (d) signaling the computer to select a desired tooth preparation shown in the three-dimensional graphic representation.

Pursuant to another feature of the present invention, a tooth preparation may be selected by an operator (e.g., a dentist) from among a set of predefined tooth preparations stored in encoded form in the computer. The computer displays the selected tooth preparation in overlay on the three-dimensional graphic representation of the tooth.

Pursuant to another feature of the present invention, the method for effecting a dental preparation includes the additional steps of cutting a tooth preparation preform corresponding to the electrically encoded tooth preparation selected via the computer and operating the computer to limit the cutting of the tooth preparation preform. An actual tooth preparation preform corresponding to the electrically encoded tooth preparation selected via the computer is then attached to the prepared tooth.

Another method for effecting a dental preparation comprises, in accordance with the present invention, the steps of (a) providing a computer with electrically encoded data specifying a three-dimensional surface of a tooth provided with a desired preparation, and (b) operating the computer to effectuate a limitation in motion of a tooth preparation instrument relative to the tooth so that the tooth is provided with the desired tooth preparation. If the tooth preparation instrument is a dentist's drill having a power supply operatively connected to the computer, the step of limiting the motion of the instrument is implemented by having the computer terminate power to the drill. Alternatively, the computer may be operated to produce a signal alerting an operator.

A method for facilitating the making of a dental preparation comprises, in accordance with the present invention, the steps of (a) providing a kit of dental preparation preforms, (b) providing a computer with a data memory loaded with electrically encoded data corresponding to all of the preforms, (c) operating the computer to select an optimal one of the preforms for a particular tooth, and (d) attaching a selected optimal one of the preforms to the tooth.

Pursuant to specific features of the present invention, the computer is provided with electrically encoded data specifying a three-dimensional surface of a tooth and is operated to display a three-dimensional graphic representation of the tooth in accordance with the electrically encoded data. The computer is then instructed to overlay at least one of the electrically encoded tooth preparation preforms on the three-dimensional graphic representation and to select an overlaid electrically encoded tooth preparation preform as the optimal one of the preforms. The selected optimal one of the preforms may then be cut, if necessary, to match the tooth upon preparation thereof.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is a perspective view of another contour data generating device usable in a dentistry system in accordance with the present invention.

DETAILED DESCRIPTION OF THE INVENTION

Figure 1:
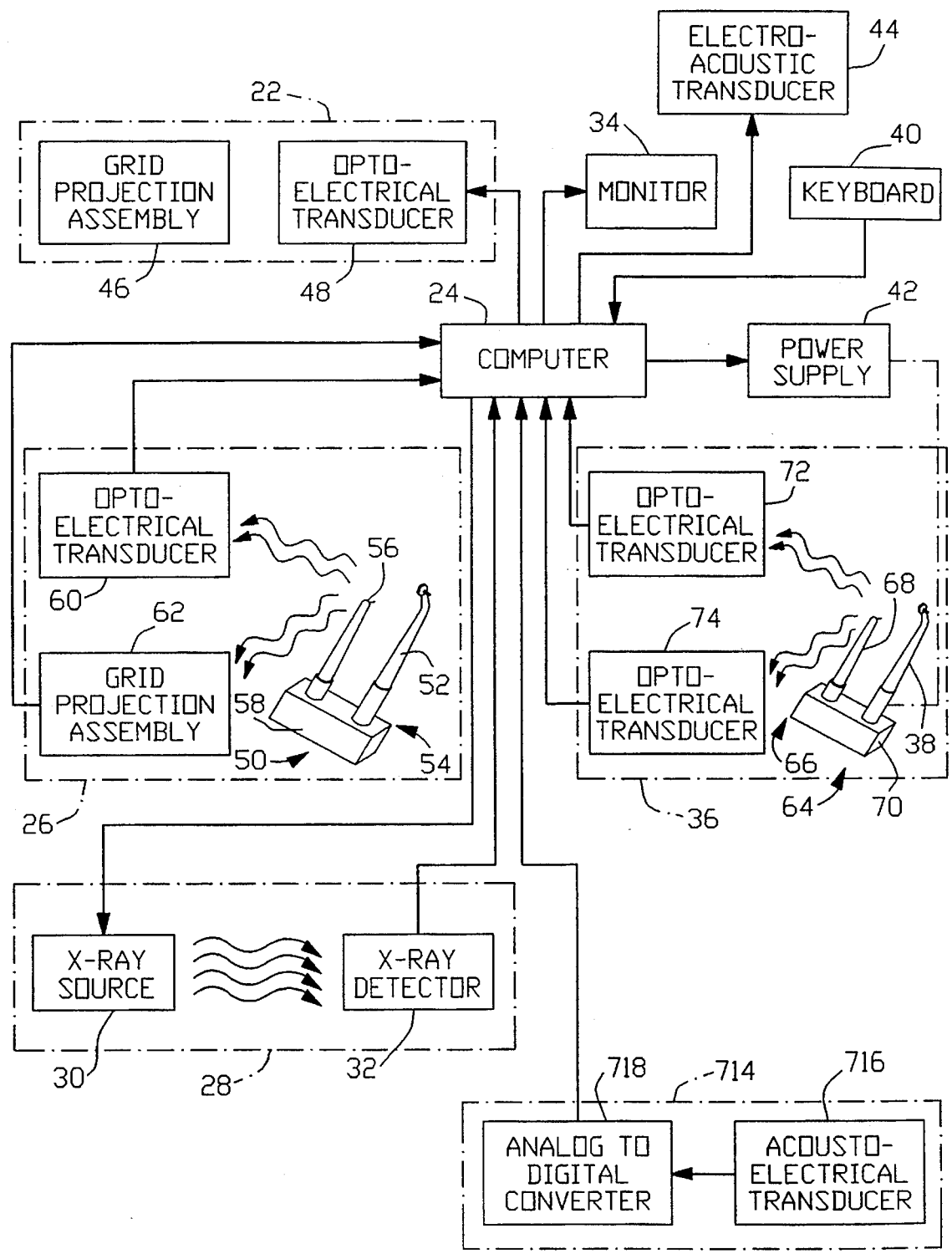
FIG. 1 is a block diagram of a system effecting a desired modification in the shape of a pre-existing object such as a tooth to which access is restricted, in accordance with the present invention.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized video signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data strem fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or to remove an outer layer of the tooth (in the case of preparing a form/shape for a crown or other prosthetic resotration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although the preferred embodiments of the present invention incorporate an optical grid, it is to be appreciated that the invention also conemplates that a grid may be imposed onto the tooth surface by other methods, such as adhesively attaching to the tooth surface a transparency provided with a grid.

As further depicted in FIG. 1 and described in detail hereinafter, data generating device 26 comprises a pantograph-type component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programmed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

In a preferred embodiment of the invention, data generating device 36 is the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
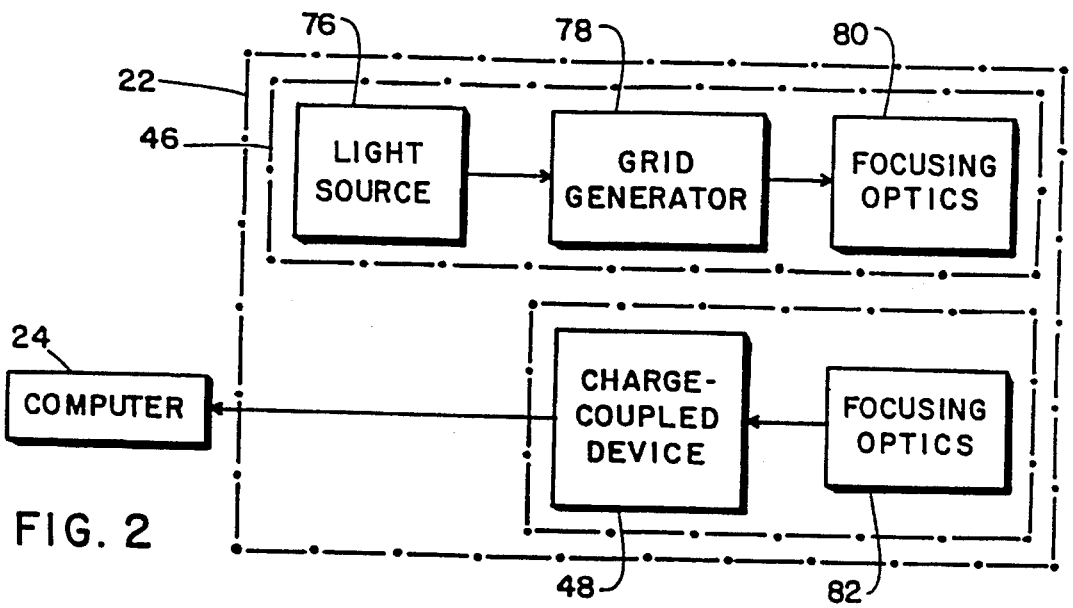
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
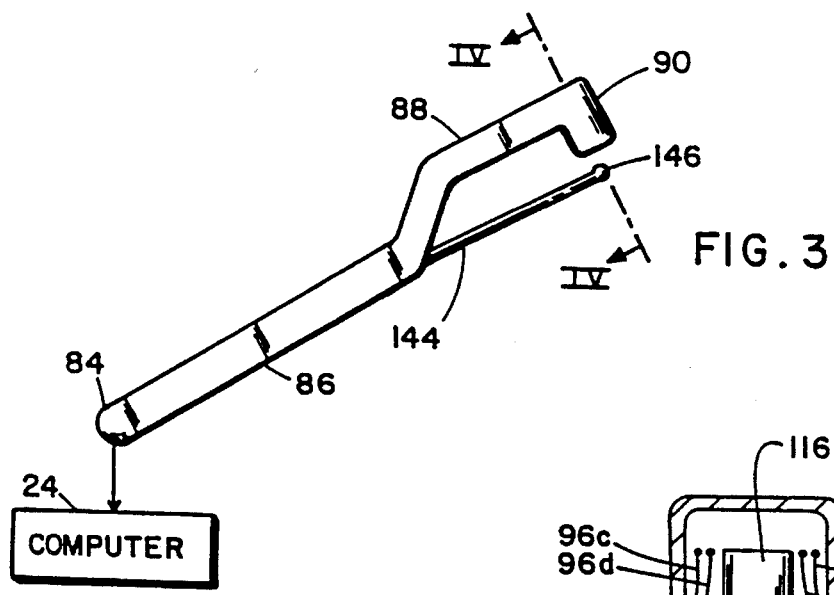
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
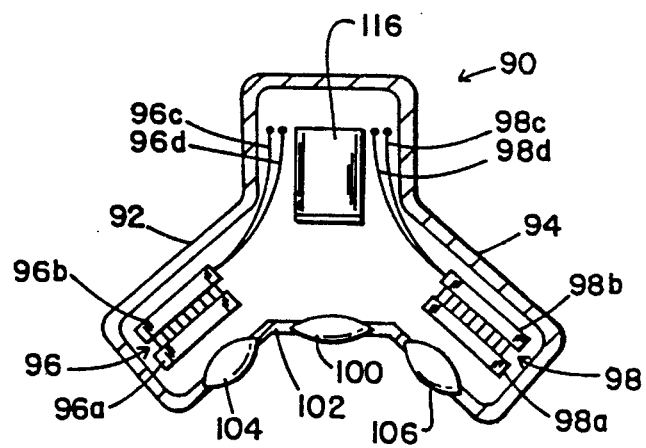
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitive sensor array 96*a* and 98*b* and respective sequencing and processing electronics 96*b* and 98*b*. The sequencing and processing electronics 96*b* and 98*b* have input and output leads 96*c*, 96*d* and 98*c*, 98*d* extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96*a* and 98*a* by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
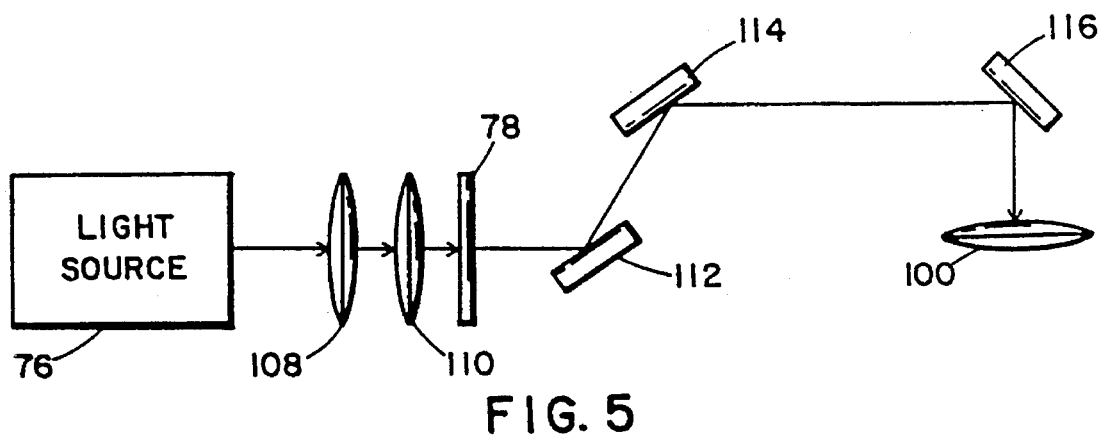
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
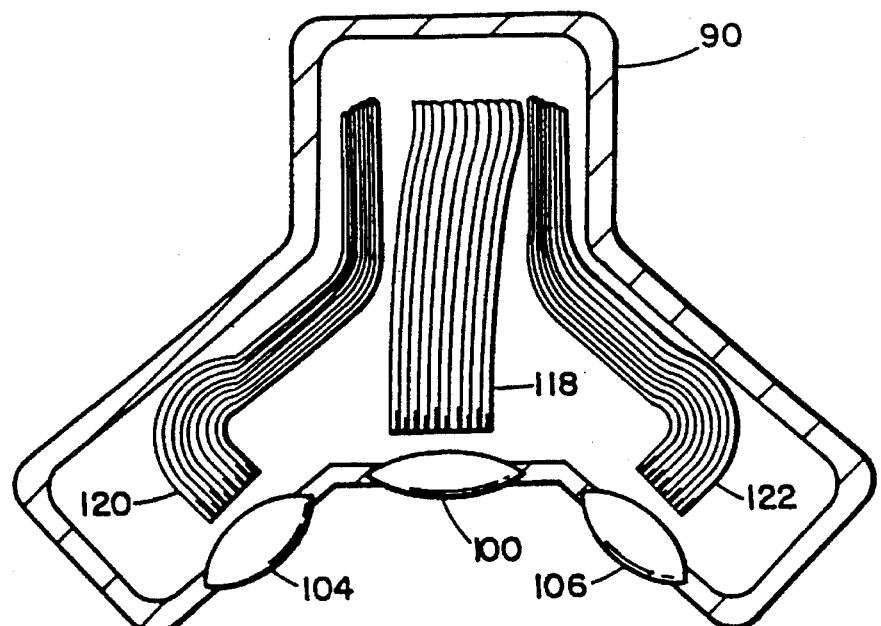
FIG. 6 is a cross-sectional view, similar to FIG. 4, of another particular embodiment of the surface data generating device of FIG. 2.

It is within the contemplation of the invention that the grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
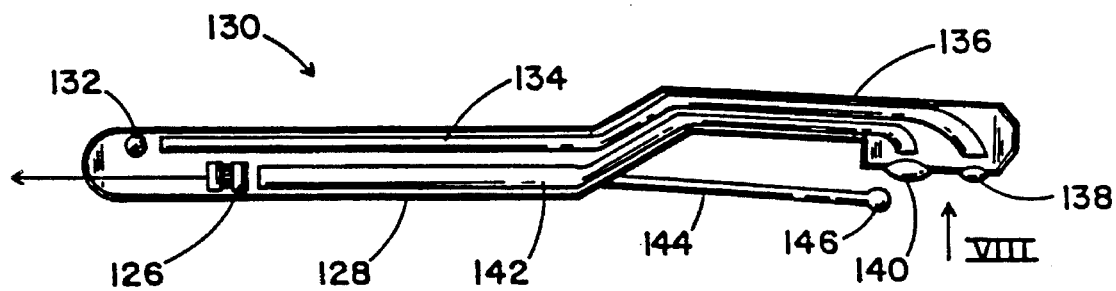
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels corresponding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises, in a preferred embodiment of the present invention, three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment of the invention, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314–324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326–336 is formed to have sufficient friction to allow the joint to hold a position once placed therein. However, the friction of each joint is low enough so that movement of the joint can be commenced fairly easily.

A plurality of digital encoders 340 are mounted to arm segments 314–324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer 24 via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
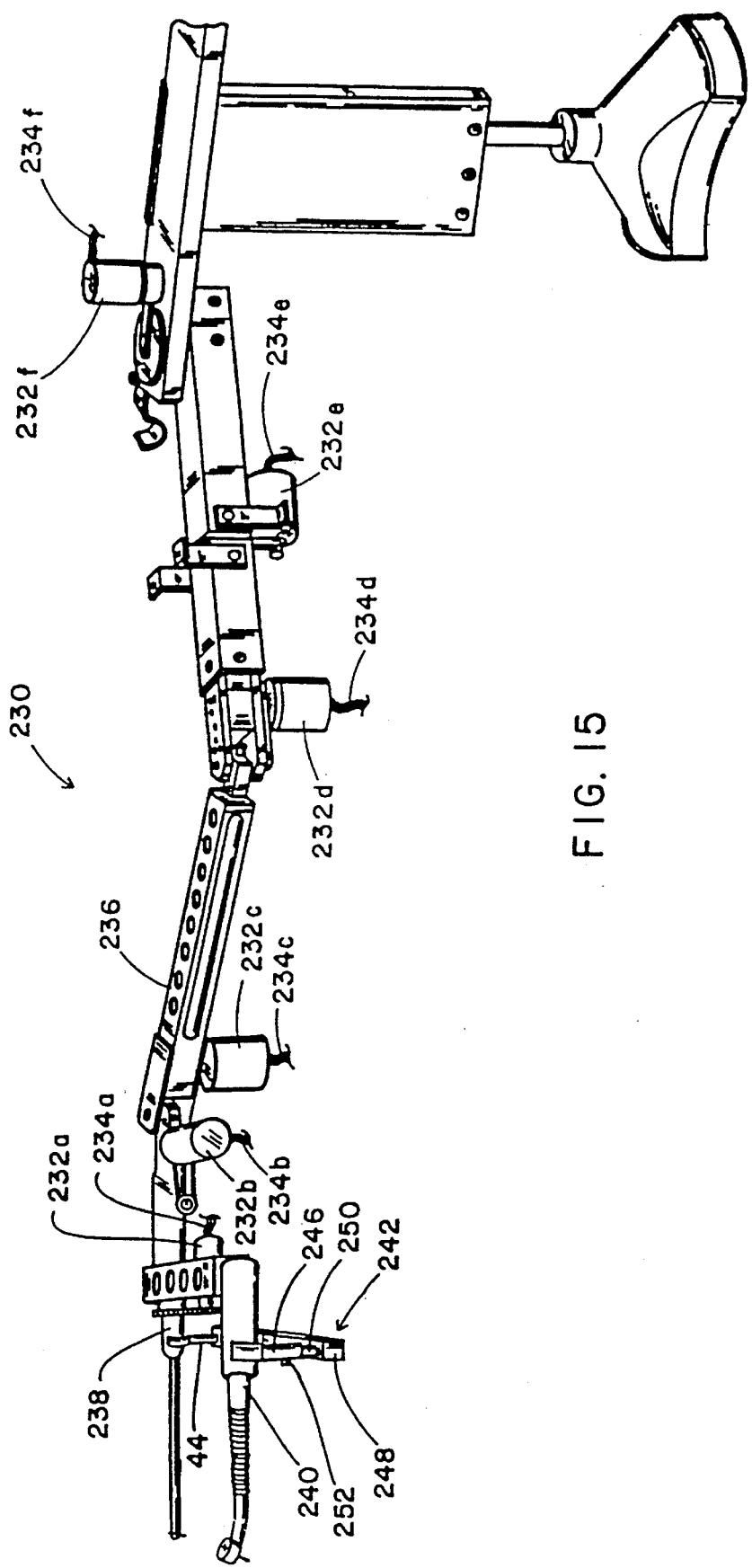
FIG. 15 is a perspective view of drill movement control assembly in accordance with a feature of the present invention.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
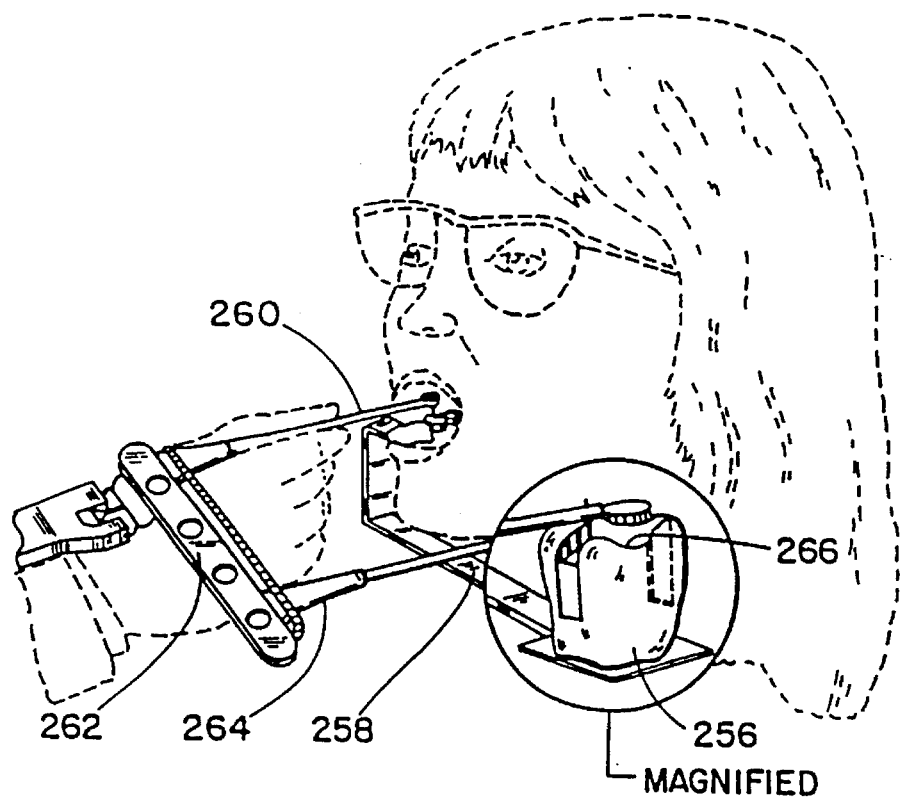
FIG. 16 is a partial perspective view, on an enlarged scale, of a drill movement restriction assembly in accordance with another feature of the present invention, showing a tooth preparation preform on an even larger scale.

Limiting the motion of a dentist's drill 254 may be accomplished, in accordance with another feature of the invention shown in FIG. 16, by selecting a tooth preparation preform 256 from a kit of preforms. Preform 256 may be selected by computer 24, as described above, to conform to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, pursuant to a particular feature of the invention, a kit is provided of dental preparation preforms in different sizes and shapes. Some preforms correspond to inlays such as that shown in FIG. 16. Other preforms correspong to onlays or crowns. The kit may also include prefabricated prosthetic devices, that is, preformed inlays and onlays for attachment to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
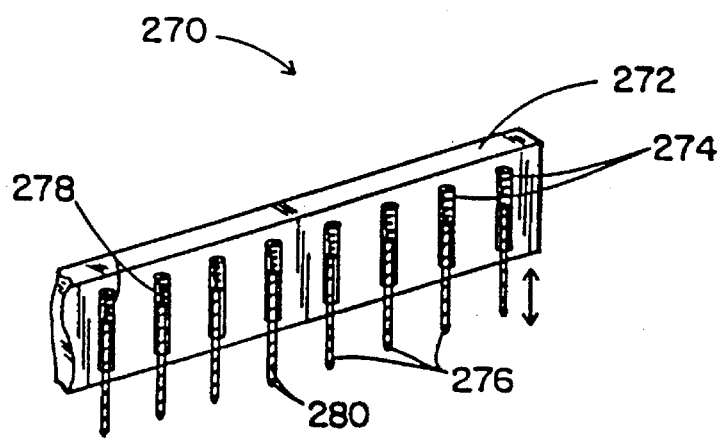
FIG. 17 is a partial schematic perspective view of a reference marker assembly in accordance with a feature of the present invention.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A system for effecting a desired modification in the shape of a pre-existing object to which access is restricted, said system comprising:

a computer;

first data input means operatively connected to said computer for providing said computer with electrically encoded data specifying a three-dimensional surface of the object;

second data input means operatively connected to said computer for providing said computer with electrically encoded data specifying a curvilinear contour of said object;

display means operatively connected to said computer for displaying a three-dimensional graphic representation of said object in response to signals generated by said computer in accordance with data from said first data input means and said second data input means;

instruction input means operatively connected to said computer for instructing said computer to modify the three-dimensional representation of said object on said display means and for selecting a modification of said three-dimensional representation which represents a desired object preparation; and output means operatively connected to said computer for issuing an output signal to effectuate a limitation in motion of a preparation instrument relative to said object so that said object is provided with said desired object preparation.

2. The system defined in claim 1 wherein said first data input means includes scanning means for optically scanning said three-dimensional surface and transmitting a video signal of said three-dimensional surface to said computer.

3. The system defined in claim 2 wherein said first data input means further includes grid means for imposing a grid on said three-dimensional surface.

4. The system defined in claim 3 wherein said grid means includes projection means for optically projecting a grid onto said three-dimensional surface.

5. The system defined in claim 4 wherein said scanning means includes two cameras.

6. The system defined in claim 5 wherein said cameras have respective optical axes disposed at an angle to one another.

7. The system defined in claim 2 wherein said first data input means further includes a manipulable instrument frame, said scanning means and said grid means being mounted to said frame.

8. The system defined in claim 7, further comprising reference means for providing said computer with a reference distance at said three-dimensional surface.

9. The system defined in claim 8 wherein said reference means includes a stylus carried by said frame at a distal end thereof.

10. The system defined in claim 9 wherein said stylus is retractably mounted to said frame.

11. The system defined in claim 2, further comprising means for providing said computer with a reference distance at said three-dimensional surface.

12. The system defined in claim 1 wherein said second data input means includes a manipulable stylus-type instrument having a distal tip engageable with said object, said second data input means further including position detection means for monitoring the location of said tip relative to said object and for feeding electrically encoded data regarding said location to said computer.

13. The system defined in claim 12 wherein said position detection means includes a pantograph extension connected to said instrument and scanning means for optically scanning the location of a point on said pantograph extension and transmitting a resulting video signal to said computer.

14. The system defined in claim 13 wherein said position detection means further includes reference means for enabling said computer to determine, via video signals from said scanning means, the location of said point on said pantograph extension relative to said object.

15. The system defined in claim 14 wherein exactly one of said reference means and said scanning means is fixed relative to said object.

16. The system defined in claim 15 wherein said reference means includes a grid fixed relative to said object.

17. The system defined in claim 15 wherein said scanning means includes a solid state optical sensor and means for fixing said sensor relative to said object.

18. The system defined in claim 13 wherein said scanning means includes at least two cameras.

19. The system defined in claim 1, further comprising a cutting instrument and position detection means for monitoring the location of a tip of said cutting instrument relative to said object and for feeding data regarding said location to said computer.

20. The system defined in claim 19 wherein said position detection means includes a pantograph extension connected to said cutting instrument and scanning means for optically scanning the location of a point on said pantograph extension and transmitting a resulting video signal to said computer.

21. The system defined in claim 20 wherein said position detection means further includes reference means for enabling said computer to determine, via video signals from said scanning means, the location of said point on said pantograph extension relative to said object.

22. The system defined in claim 21 wherein said reference means includes a grid fixed relative to said object.

23. The system defined in claim 20 wherein said scanning means includes at least two cameras.

24. The system defined in claim 20 wherein said scanning means includes a solid state optical sensor and means for fixing said sensor relative to said object.

25. The system defined in claim 1 wherein said display means includes a two-dimensional screen.

26. The system defined in claim 25 wherein said display means includes means for holographically projecting an image.

27. The system defined in claim 1 wherein said instruction input means includes a cutting instrument and position detection means for monitoring the location of a tip of said cutting instrument relative to said object and for feeding data regarding said location to said computer.

28. The system defined in claim 1 wherein said instruction input means includes a keyboard connected to said computer.

29. The system defined in claim 1 wherein said instruction input means includes a contact sensitive region of said display means.

30. The system defined in claim 1, further comprising a cutting instrument having a power supply operatively connected to said computer and locator means for determining the location of an operating tip of said cutting instrument relative to said object, said output means including means for terminating power to said cutting instrument.

31. The system defined in claim 1, further comprising a cutting instrument and actuator means for automatically moving said cutting means in three dimensions under the control of said computer, said output means including circuit means operatively connected to said actuator means for controlling said actuator means to move said cutting means.

32. The system defined in claim 1 wherein said output means includes indicator means for producing an alert signal to an operator.

33. The system defined in claim 1, further comprising third data input means operatively connected to said computer for providing said computer with electrically encoded data specifying an internal structural feature of said object.

34. The system defined in claim 33 wherein said third data input means includes an X-ray device.

35. The system defined in claim 1 wherein said object is a tooth and the system is directed to preparing said tooth for a filling, inlay or crown.

36. A dentistry system comprising:

a computer;

data input means operatively connected to said computer for providing said computer with electrically encoded data specifying a three-dimensional surface of a tooth;

display means operatively connected to said computer for displaying a three-dimensional graphic representation of said tooth in response to signals generated by said computer in accordance with data from said data input means; and instruction input means operatively connected to said computer for instructing said computer to modify the three-dimensional representation of said tooth on said display means and for selecting a modification of said three-dimensional representation which represents a desired tooth preparation, said instruction input means including a manipulable dentist's drill and position detection means for monitoring the location of a tip of said drill relative to said tooth and for feeding data regarding said location to said computer.

37. The dentistry system defined in claim 36 wherein said instruction input means includes a keyboard connected to said computer.

38. The dentistry system defined in claim 36 wherein said instruction input means includes a contact sensitive region of said display means.

39. A method for effecting a desired modification in the shape of a pre-existing object to which access is restricted by other formations, comprising the steps of:

generating electrically encoded data specifying a three-dimensional surface of the object;

transmitting said electrically encoded data to a computer loaded with a stereophotogrammetic triangulation program;

generating electrically encoded data specifying a curvilinear contour of said object;

transmitting the electrically encoded data specifying the curvilinear contour to said computer;

operating said computer to display a three-dimensional graphic representation of said object in accordance with the electrically encoded data specifying said three-dimensional surface and said curvilinear contour;

instructing said computer to modify the three-dimensional representation of said object to show an object preparation;

signaling said computer to select a desired object preparation shown in said three-dimensional graphic representation; and operating said computer to generate an output signal to effectuate a limitation in motion of a preparation instrument relative to said object so that said object is provided with said desired object preparation.

40. The method defined in claim 39 wherein said step of generating electrically encoded data specifying a three-dimensional surface of the object includes the step of optically scanning said three-dimensional surface.

41. The method defined in claim 40 wherein the step of transmitting electrically encoded data specifying a three-dimensional surface of the object includes the transmission of a video signal of said three-dimensional surface to said computer.

42. The method defined in claim 41 wherein said step of generating electrically encoded data specifying a three-dimensional surface of the object includes the step of imposing a grid on said three-dimensional surface.

43. The method defined in claim 42 wherein said step of imposing a grid includes the step of optically projecting a grid onto said three-dimensional surface.

44. The method defined in claim 39, further comprising the step of providing said computer with a reference distance at said three-dimensional surface.

45. The method defined in claim 39 wherein said step of generating electrically encoded data specifying a curvilinear contour of said object includes the step of tracing said curvilinear contour with a manipulable stylus-type instrument having a distal tip engageable with said object, further comprising the steps of monitoring the location of said tip relative to said object and feeding electrically encoded data regarding said location to said computer.

46. The method defined in claim 45 wherein said step of monitoring includes the step of optically scanning the location of a point on a pantograph extension connected to said instrument, said step of feeding including the step of transmitting a resulting video signal to said computer.

47. The method defined in claim 46 wherein said step of monitoring includes the step of providing a reference frame for enabling said computer to determine, via said resulting video signal, the location of said point on said pantograph extension relative to said object.

48. The method defined in claim 46, wherein said object is a tooth, further comprising the step of fixing exactly one of said reference frame and a video signal generator to the patient's jaw wherein said object is rooted.

49. The method defined in claim 48 wherein said reference frame includes a grid.

50. The method defined in claim 46 wherein said step of optically scanning includes the step of operating a solid state optical sensor, further comprising the step of fixing said sensor relative to the object.

51. The method defined in claim 39, further comprising the steps of cutting said object with a cutting instrument, monitoring the location of a tip of said cutting instrument relative to said object, and feeding data regarding said location to said computer.

52. The method defined in claim 51 wherein said step of monitoring includes the steps of monitoring a pantograph extension connected to said cutting instrument and optically scanning the location of a point on said pantograph extension, said step of feeding including the step of transmitting a resulting video signal to said computer.

53. The method defined in claim 52, further comprising the step of providing a reference frame for enabling said computer to determine, via said resulting video signal, the location of said point on said pantograph extension relative to said object.

54. The method defined in claim 53 wherein said reference frame includes a grid.

55. The method defined in claim 54, further comprising the step of fixing said grid relative to said object.

56. The method defined in claim 52 wherein said step of scanning is implemented by operating a solid state optical sensor, further comprising the step of fixing said sensor relative to said object.

57. The method defined in claim 39 wherein said step of instructing includes the steps of cutting an incision into said object with a cutting instrument, monitoring the location of a tip of said cutting instrument relative to said object, and feeding data regarding said location to said computer.

58. The method defined in claim 39 wherein said step of instructing includes the step of operating said computer to select an object preparation from among a set of predefined object preparations stored in encoded form in said computer.

59. The method defined in claim 58 wherein said step of instructing further includes the step of operating said computer to display the selected object preparation preform in overlay on the three-dimensional graphic representation of said object.

60. The method defined in claim 39 wherein said step of instructing includes the step of entering commands via a keyboard connected to said computer.

61. The method defined in claim 39 wherein said step of instructing includes the step of touching a contact sensitive region of a display device operatively connected to said computer.

62. The method defined in claim 39 wherein said step of instructing includes the step of operating a mouse device operatively connected to said computer.

63. The method defined in claim 39, further comprising the steps of operating a cutting instrument having a power supply operatively connected to said computer and monitoring the location of a cutting tip of said instrument relative to said object, said step of operating said computer to generate an output signal including the step of terminating power to said instrument.

64. The method defined in claim 39, further comprising the step of manually operating a cutting instrument, said step of operating said computer to generate an output signal including the step of producing an alert signal to an operator.

65. The method defined in claim 39, further comprising the step of providing said computer with electrically encoded data specifying an internal structural feature of the said object.

66. The method defined in claim 65 wherein said step of providing said computer with electrically encoded data specifying an internal structural feature of said object includes operating an X-ray device.

67. A method for effecting a dental preparation, comprising the steps of:

providing a computer with electrically encoded data specifying a three-dimensional surface of a tooth;

operating said computer display a three-dimensional graphic representation of said tooth in accordance with said electrically encoded data;

instructing said computer to modify the three-dimensional representation of said tooth on said display means to show a tooth preparation; and signaling said computer to select a desired tooth preparation shown in said three-dimensional graphic representation, said step of instructing including the step of operating said computer to select a tooth preparation from among a set of predefined tooth preparations stored in encoded form in said computer.

68. The method defined in claim 67 wherein said step of instructing further includes the step of operating said computer to display the selected tooth preparation in overlay on the three-dimensional graphic representation of said tooth.

69. The method defined in claim 67, further comprising the steps of cutting a tooth preparation preform corresponding to the electrically encoded tooth preparation selected via said computer, operating said computer to limit the cutting of said tooth preparation preform.

70. The method defined in claim 67, further comprising the step of attaching to said tooth an actual tooth preparation preform corresponding to the electrically encoded tooth preparation selected via said computer.

71. The method defined in claim 67, further comprising the step of operating said computer to generate an output signal to effectuate a limitation in motion of a tooth preparation instrument relative to said tooth so that said tooth is provided with said desired tooth preparation.

72. A system for effecting a desired modification in the shape of a pre-existing object to which access is restricted, said system comprising:

a computer;

first data input means operatively connected to said computer for providing said computer with electrically encoded data specifying a three-dimensional surface of the object;

second data input means operatively connected to said computer for providing said computer with electrically encoded data specifying a curvilinear contour of said object; and display means operatively connected to said computer for displaying a three-dimensional graphic representation of said object in response to signals generated by said computer in accordance with data from said first data input means and said second data input means.

73. The system defined in claim 72, further comprising instruction input means operatively connected to said computer for instructing said computer to modify the three-dimensional representation of said object on said display means and for selecting a modification of said three-dimensional representation which represents a desired object preparation.

74. The system defined in claim 73, further comprising output means operatively connected to said computer for issuing an output signal to effectuate a limitation in motion of a preparation instrument relative to said object so that said object is provided with said desired object preparation.

75. The system defined in claim 72 wherein said first data input means includes scanning means for optically scanning said three-dimensional surface and transmitting a video signal of said three-dimensional surface to said computer.

76. The system defined in claim 72 wherein said second data input means includes a manipulable stylus-type instrument having a distal tip engageable with said object, said second data input means further including position detection means for monitoring the location of said tip relative to said object and for feeding electrically encoded data regarding said location to said computer.

77. A method for effecting a dental preparation, comprising the steps of:

providing a computer with electrically encoded data specifying a three-dimensional surface of a tooth;

operating said computer display a three-dimensional graphic representation of said tooth in accordance with said electrically encoded data;

instructing said computer to modify the three-dimensional representation of said tooth on said display means to show a tooth preparation;

signaling said computer to select a desired tooth preparation shown in said three-dimensional graphic representation; and operating said computer to generate an output signal to effectuate a limitation in motion of a tooth preparation instrument relative to said tooth so that said tooth is provided with said desired tooth preparation.

* * * * *